US00PP31378P2

(12) United States Plant Patent
Pierron-Darbonne

(10) Patent No.: US PP31,378 P2
(45) Date of Patent: Jan. 21, 2020

(54) BLUEBERRY PLANT NAMED 'PLABLUE 1549'

(50) Latin Name: *Vaccinium corymbosum*
Varietal Denomination: Plablue 1549

(71) Applicant: Plantas de Navarra, S.A. Sociedad Unipersonal, Navarra (ES)

(72) Inventor: Alexandre Pierron-Darbonne, Pamplona (ES)

(73) Assignee: Plantas de Navarra, S.A. Sociedad Unipersonal (ES)

( * ) Notice: Subject to any disclaimer, the term of this patent is extended or adjusted under 35 U.S.C. 154(b) by 0 days.

(21) Appl. No.: 16/501,259

(22) Filed: Mar. 13, 2019

(30) Foreign Application Priority Data

Aug. 9, 2018 (QZ) ..... PBR 2018/2074

(51) Int. Cl.
*A01H 5/08* (2018.01)
*A01H 6/36* (2018.01)

(52) U.S. Cl.
USPC ..... Plt./157

(58) Field of Classification Search
USPC ..... Plt./156, 157
See application file for complete search history.

*Primary Examiner* — Susan McCormick Ewoldt
*Assistant Examiner* — Karen M Redden
(74) *Attorney, Agent, or Firm* — Knobbe, Martens, Olson & Bear, LLP

(57) ABSTRACT

Described is a new and distinct blueberry variety with varietal denomination 'Plablue 1549', characterized by a combination of traits which include, upright plant growth habit, and very abundant production of medium fruit-size, round shaped and very firm fruit. 'Plablue 1549' is a self-fertile variety.

17 Drawing Sheets

Botanical classification: *Vaccinium corymbosum* L.

Variety denomination: The new plant has the varietal denomination 'Plablue 1549'.

CROSS-REFERENCE TO RELATED APPLICATIONS

This application claims the benefit of European Community Plant Variety Office Application No. 2018/2074, for a blueberry variety named 'Plablue 1549,' filed on Aug. 9, 2018, the entirety of which is incorporated by reference herein.

BACKGROUND

Disclosed herein is a new and distinct southern highbush blueberry variety (*Vaccinium corymbosum* L.). The varietal denomination of the new variety is 'Plablue 1549.' The new variety of blueberry was created in a breeding program by crossing two parents; in particular, by crossing as seed parent an undistributed blueberry parent designated 14.028.001 (unpatented) and as pollen parent an undistributed blueberry parent designated 14.026.001 (unpatented). Female and male are selections from breeder's program of the applicant. Both parental varieties are property of the applicant and have not been commercialized.

The new variety was grown and asexually propagated by softwood cuttings in Segovia, Spain, 3° 59'W., 41° 22'N., 2742 feet elevation. Clones of the new variety were further asexually propagated and extensively tested. This propagation and testing has demonstrated that the combination of traits disclosed herein which characterize the new variety are fixed and retained true to type through successive generations of asexual reproduction.

The growing period in Huelva, Spain, where the observations on primocane production were made, is between about November 20 and June 22 of the following year.

SUMMARY

The present invention relates to a new and distinct southern highbush blueberry variety. The varietal denomination of the new variety is 'Plablue 1549', that produces and maintains a medium vigorous plant with consistent fruit production from beginning January through middle June. Among the characteristics which appear to distinguish the new variety from other varieties are a combination of traits which include an upright plant growth habit, and very abundant production of medium fruit-size, round shaped and very firm fruit.

The new blueberry plant variety 'Plablue 1549' has not been observed under all possible environmental conditions. The phenotype may vary somewhat with variations in environmental and cultural practices such as temperature and light intensity without, however, any variance in genotype.

COMPARISON TO THE PARENTS

The new variety is distinguished from its parents by the following characteristics which are different than the seed parent designated '14.028.001' (unpatented) and the pollen parent designated '14.026.001' (unpatented).

Size of corolla tube in the flower of seed parent '14.028.001' (unpatented) is smaller than in the flower of 'Plablue 1549'.

Shape of corolla of flower of seed parent '14.028.001 (unpatented) is cylindrical, whereas shape of corolla of flower of 'Plablue 1549' is urceolate.

Seed parent '14.028.001' (unpatented) shows an oblate shape fruit, whereas 'Plablue 1549' shows a round shape fruit.

Calyx basin of fruit of seed parent '14.28.001' (unpatented) is shallow, whereas the calyx basin of fruit of 'Plablue 1549' has a medium depth.

Shape of leaf of pollen parent '14.026.001' (unpatented) is lanceolate, whereas the shape of leaf of 'Plablue 1549' is elliptic.

Shape of corolla of the flower of pollen parent '14.026.001 (unpatented) is cylindrical, whereas shape of corolla of the flower of 'Plablue 1549' is urceolate.

Pollen parent '14.026.001' (unpatented) shows an oblate shape fruit, whereas 'Plablue 1549' shows a round shape fruit.

COMPARISON TO CLOSEST VARIETY

The new variety is closest to the variety 'Biloxi' (unpatented), but is distinguished therefrom by the following characteristics which are different than 'Biloxi'.

Plant of 'Biloxi' (unpatented) exhibits a weak vigor and a semi upright habit, whereas the plant of 'Plablue 1549' exhibits a medium vigor and an upright growth habit.

Ratio length/width of leaf of 'Biloxi' (unpatented) is longer than the ratio length/width of leaf of 'Plablue 1549'.

Density of fruit cluster of 'Biloxi' (unpatented) is higher than the density of fruit cluster of 'Plablue 1549'.

Fruit shape of 'Biloxi' (unpatented) is oblate, whereas in 'Plablue 1549' fruit shape is round.

Fruit of 'Biloxi' (unpatented) shows a soft firmness, whereas the fruit of 'Plablue 1549' shows a very firm firmness.

Depth of calyx basin in the fruit of 'Biloxi' (unpatented) is shallow, whereas depth of calyx in the fruit of 'Plablue 1549' is medium.

Time of beginning of flowering on one-year-old shoot of 'Biloxi' (unpatented) is less early than in 'Plablue 1549'

Time of beginning of fruit ripening on one-year-old shoot of 'Biloxi' (unpatented) is less early than in 'Plablue 1549'.

Difference in vigor and grow habit of 'Plablue 1549' (designated 15.10.086) and 'Biloxi' (unpatented) are shown in FIG. 1 and FIG. 13. Differences in the ratio of length/width of the leaf of 'Plablue 1549' (designated 15.10.086) and 'Biloxi' (unpatented) are shown in FIG. 3 and FIG. 14. Differences in density of fruit cluster of 'Plablue 1549' (designated 15.10.086) and 'Biloxi' (unpatented) are shown in FIG. 8 and FIG. 15. Differences in fruit shape of 'Plablue 1549' (designated 15.10.086) and 'Biloxi' (unpatented) are shown in FIG. 9 and FIG. 16. Differences in depth of calyx basin in the fruit of 'Plablue 1549' (designated 15.10.086) and fruit of 'Biloxi' (unpatented) are shown in FIG. 11 and FIG. 17. These differences are maintained during the harvest season.

BRIEF DESCRIPTION OF THE ILLUSTRATIONS

The accompanying photographs show typical specimens of the new variety, designated 15.10.086 in the illustrations, including fruit, foliage and flower, in color as nearly true as it is reasonably possible to make in color illustrations of this character.

The plants depicted in the drawings were planted October 14 in the farm of La Mogalla in Cartaya (Huelva), Spain, about 7° W, 37° N, 45 feet elevation.

Drawings/photographs were taken April (about April 4 and April 12): minimum temperate about 7° to 9° Centigrade, maximum temperate about 18 to 22° Centigrade.

FIG. 1 and FIG. 2 show several plants of the new variety (designated 15.10.086) which exhibit a upright habit plant with several clusters of violet-blue color fruit (RHS Violet-Blue group color near 97 D to 97 C) with wax and rounded shape fruits.

FIG. 3 and FIG. 4 show the upper side and the underside, respectively, of a complete leaf of the new variety (designated 15.10.086) with elliptic shape. In it, we can see that the leaf color of upper side of the leaf of the new variety (designated 15.10.086) is a green color (RHS Green group near 137 C to 137 A) and the leaf color of underside of the leaf of the new variety (designated 15.10.086) is a yellow-green color (RHS Yellow-Green group color near 144 B to 144 A).

FIG. 5 shows clusters with immature flowers of the new variety (designated 15.10.086). In it, we can see the immature flower red color (RHS Orange-Red group color near 35 B to 35 A).

FIG. 6 shows typical flower of the new variety (designated 15.10.086). In it, we can see the corolla of the new variety (designated 15.10.086) with white color (RHS Yellow-White group color near 158 C to 158 B).

DESCRIPTION OF THE NEW VARIETY

Figure 1:
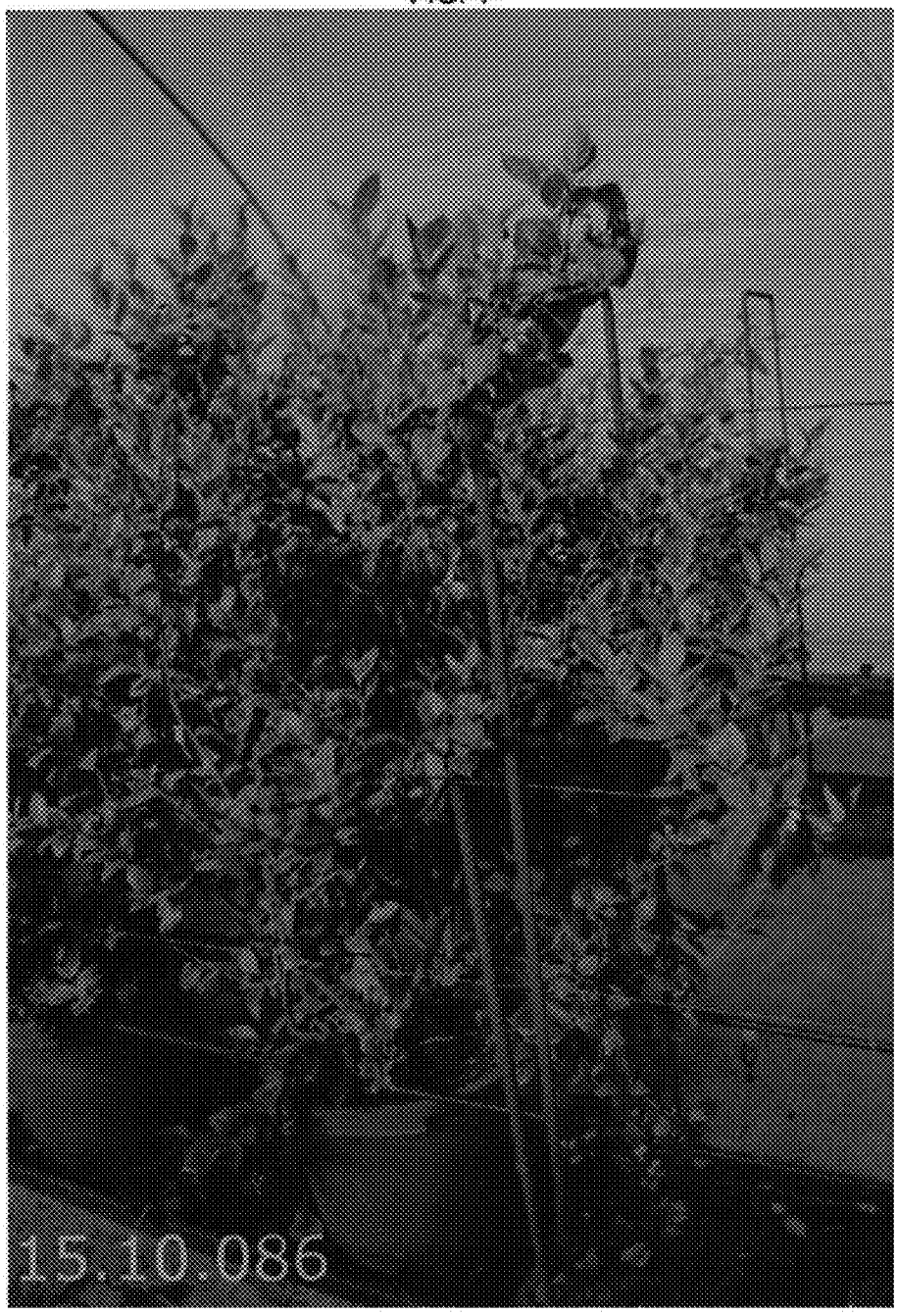
Figure 2:
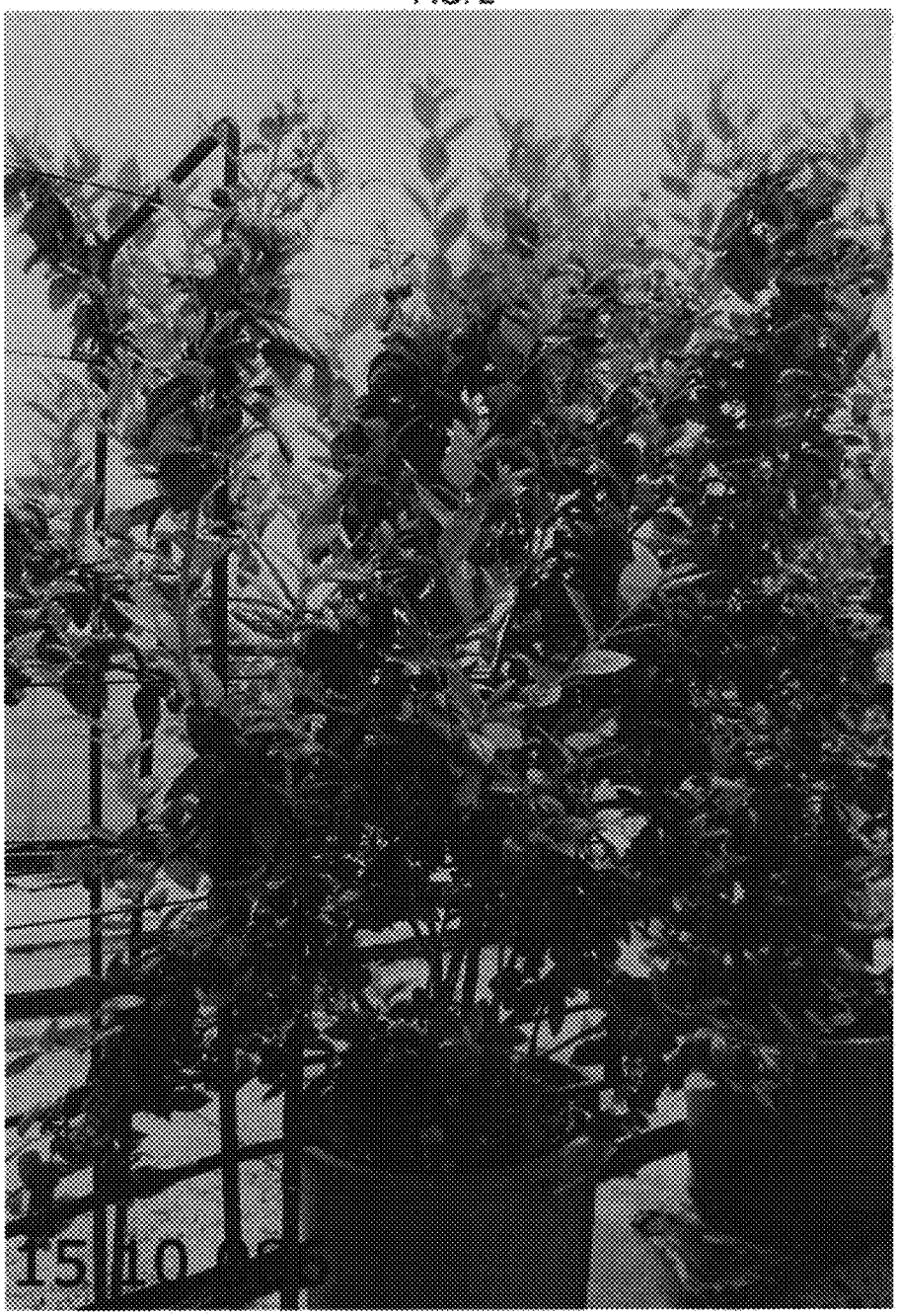
Figure 3:
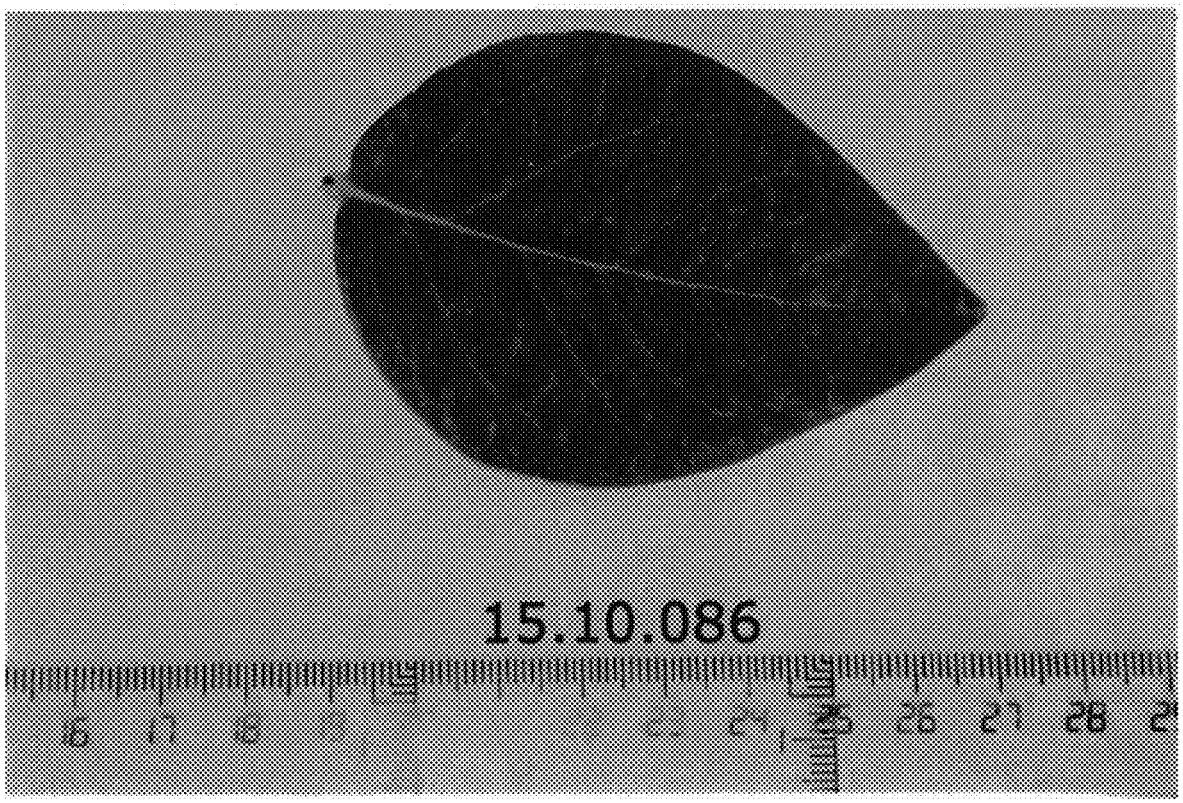
Figure 4:
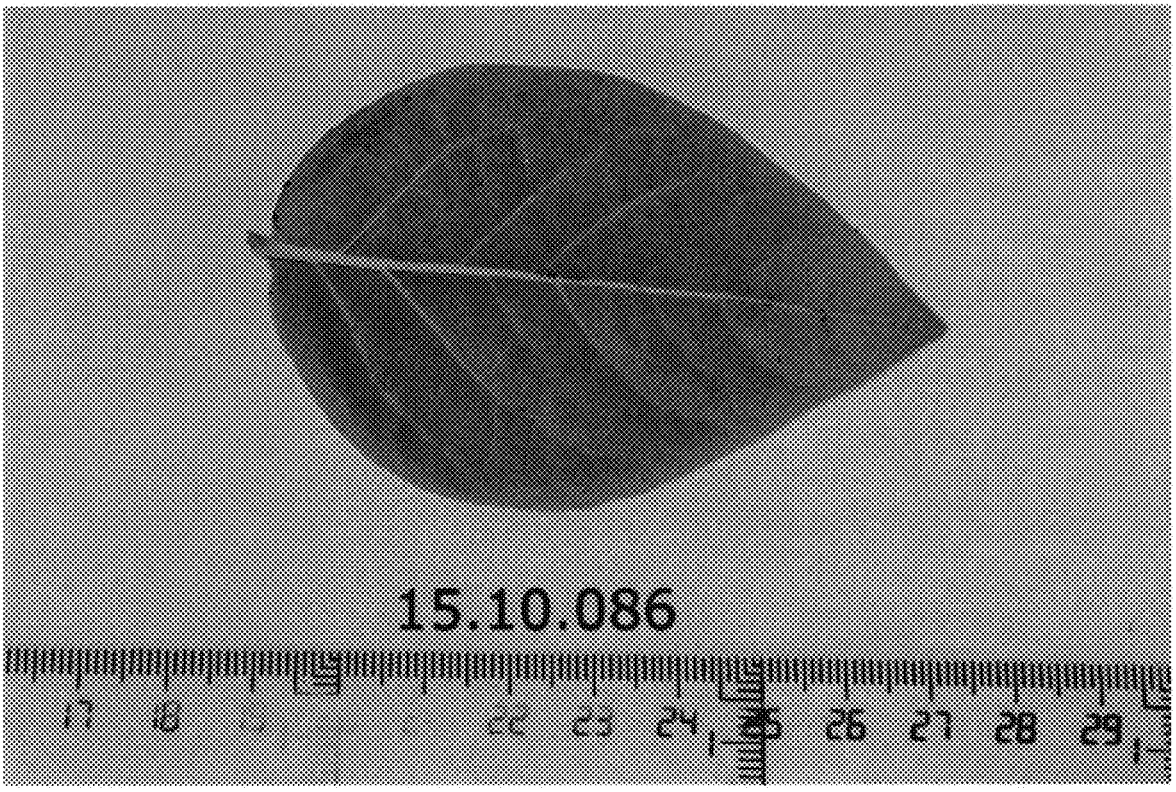
Figure 5:
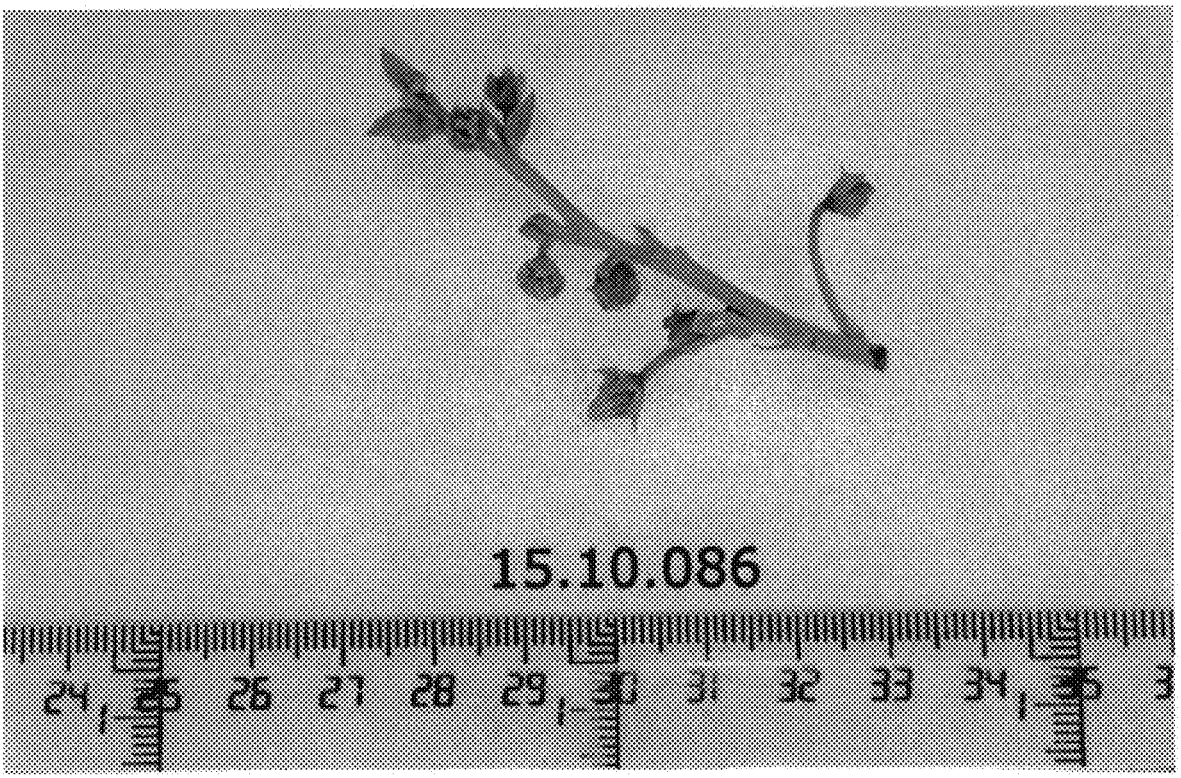
Figure 6:
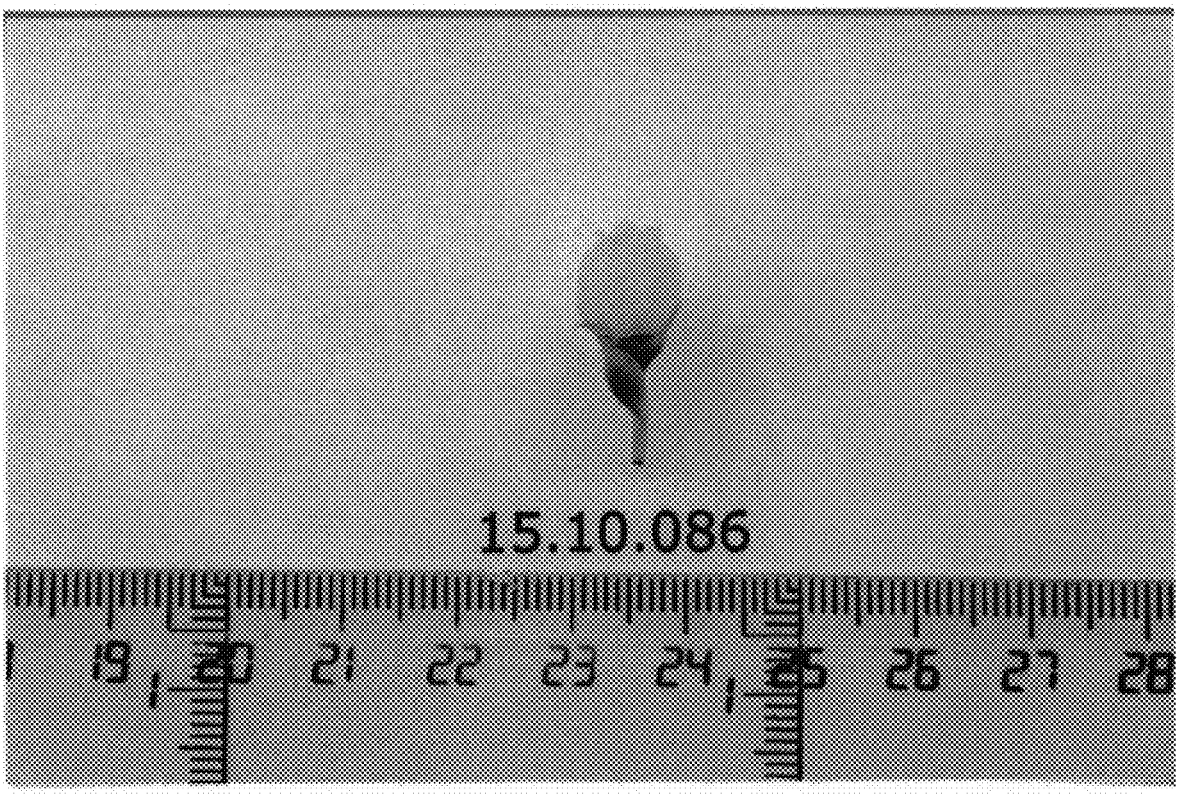
Figure 7:
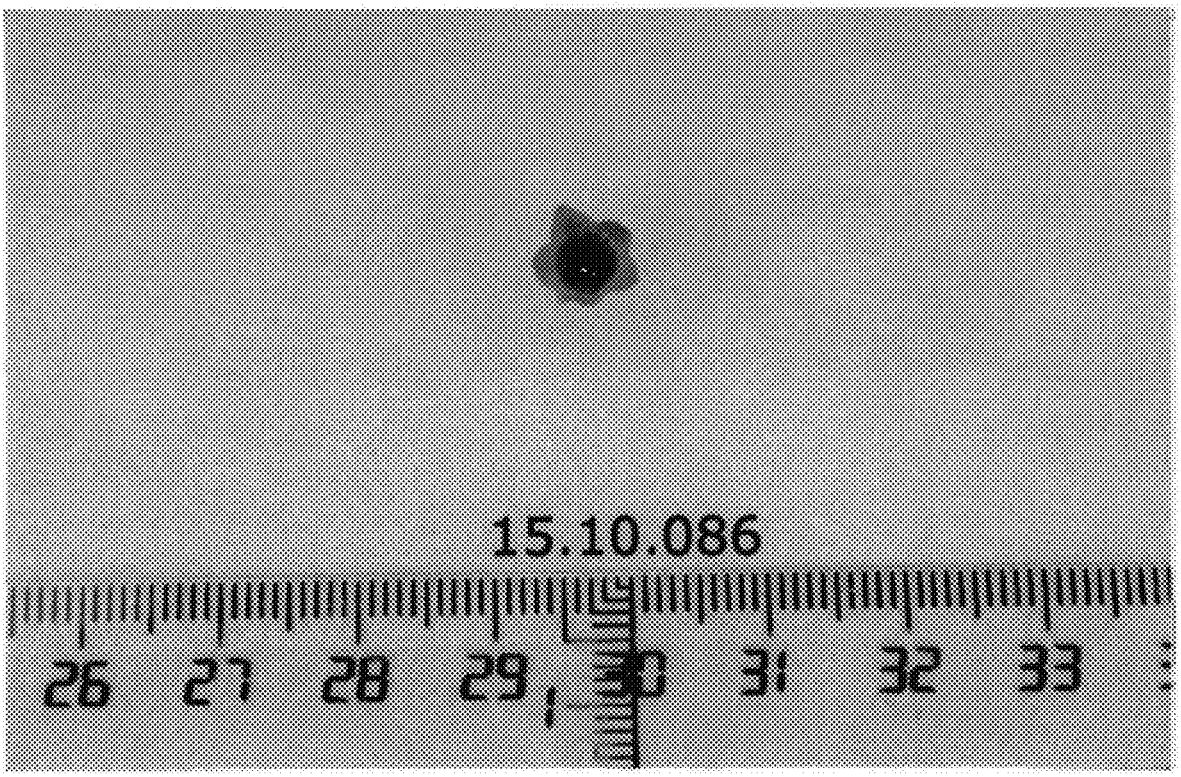
FIG. 7 shows typical sepals of the new variety (designated 15.10.086) with yellow-green color (RHS Yellow-Green group color near 145 B to 145 A).
Figure 8:
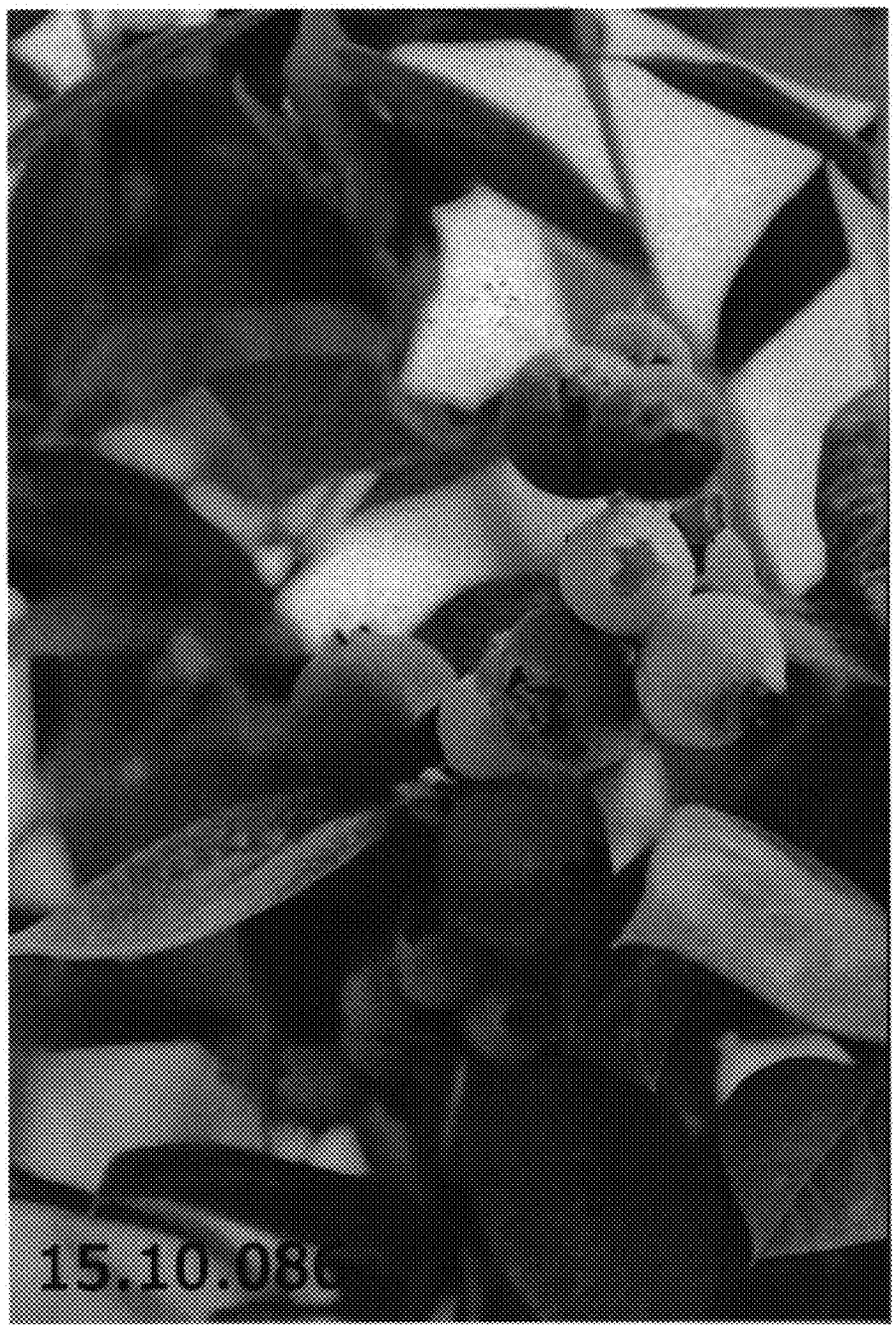
FIG. 8 shows the density of fruit cluster of the new variety (designated 15.10.086).
Figure 9:
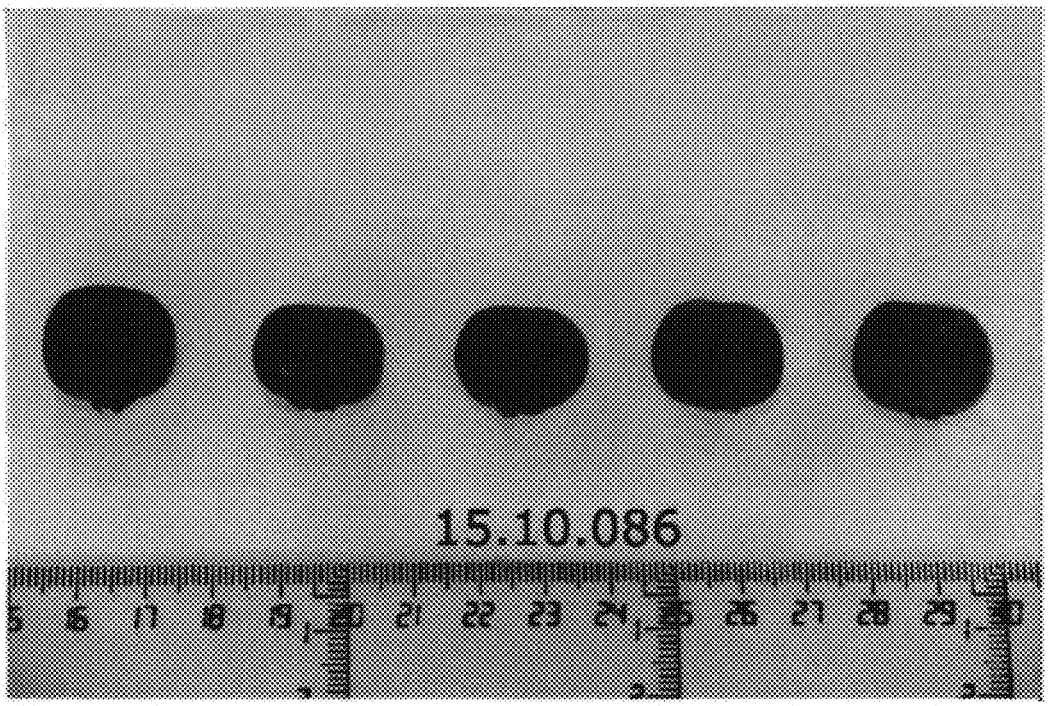
FIG. 9 and FIG. 10 show typical fruits of the new variety (designated 15.10.086) with round shape and violet-blue color with wax (RHS Violet-Blue group color near 97 D to 97 C).
Figure 10:
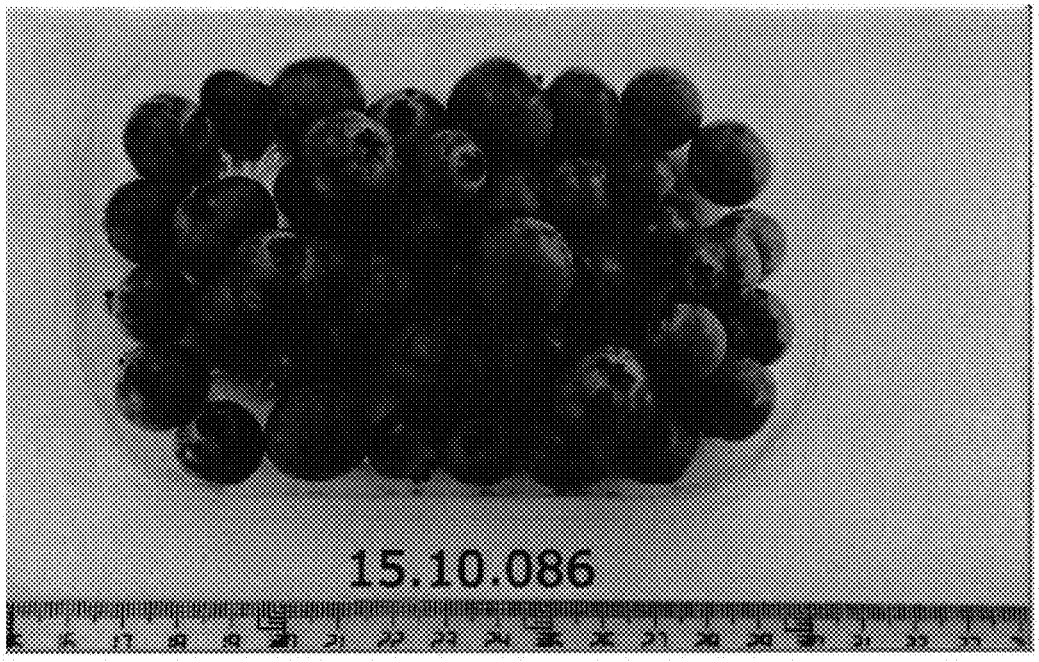
Figure 11:
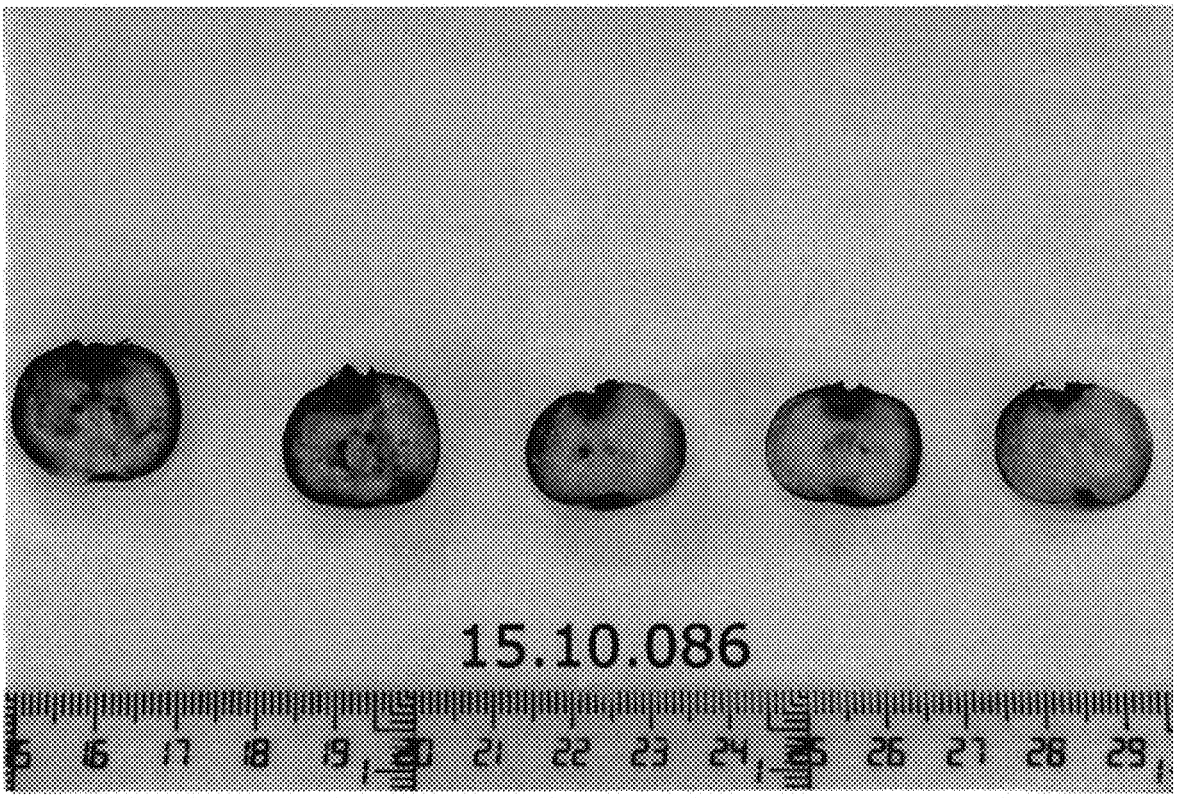
FIG. 11 shows typical sliced fruits of the new variety (designated 15.10.086) with yellow-green flesh color (RHS Yellow-Green group color near 149 D to 149 C).
Figure 12:
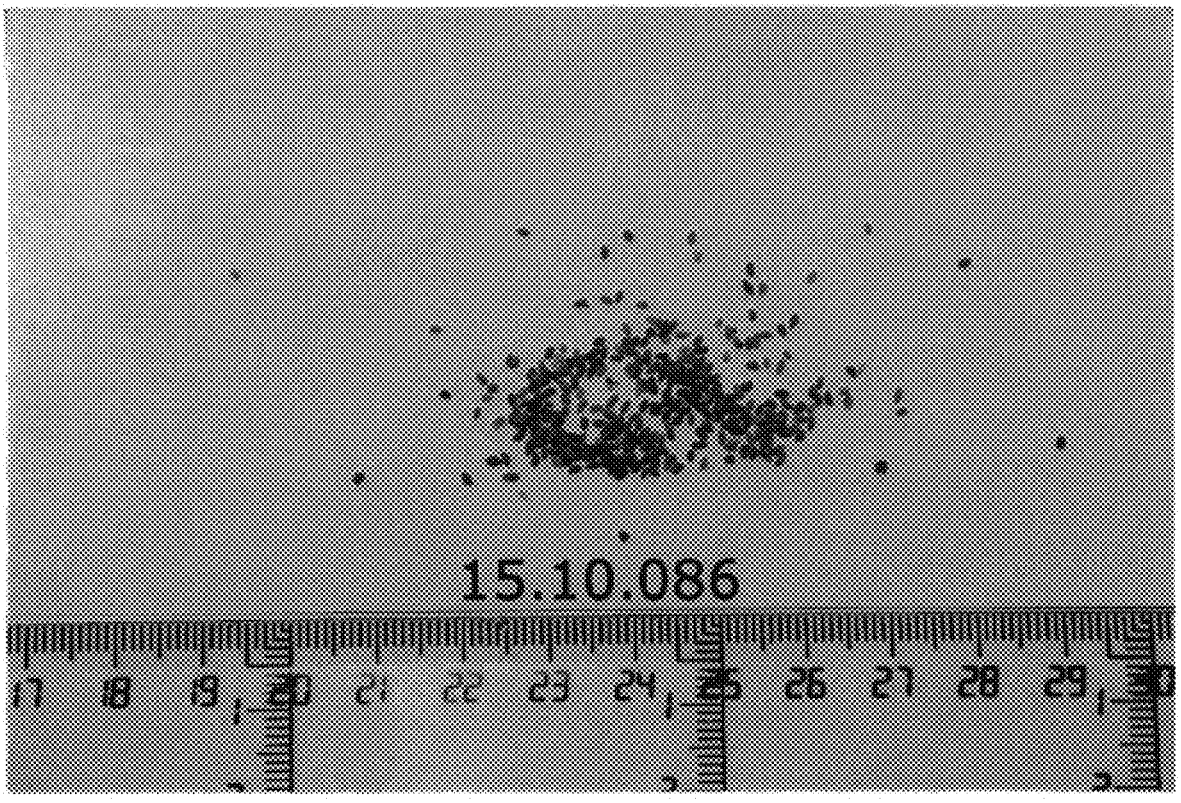
FIG. 12 shows typical seeds of the new variety (designated 15.10.086) with greyed-orange color (RHS Greyed-Orange group color near 165 B to 165 A).
Figure 13:
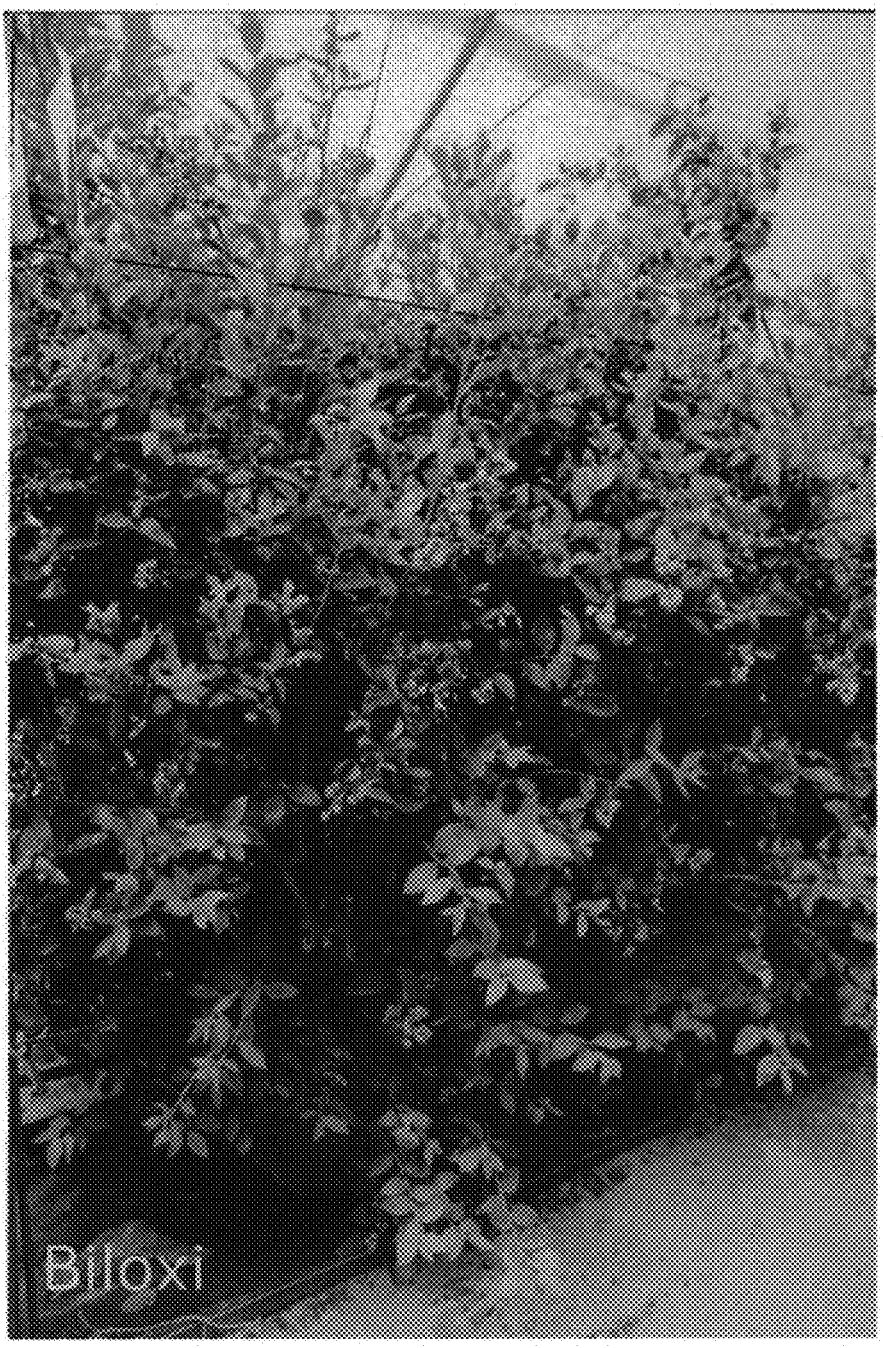
FIG. 13 shows several plants of the blueberry variety 'Biloxi' (unpatented) which exhibits a semi upright habit.
Figure 14:
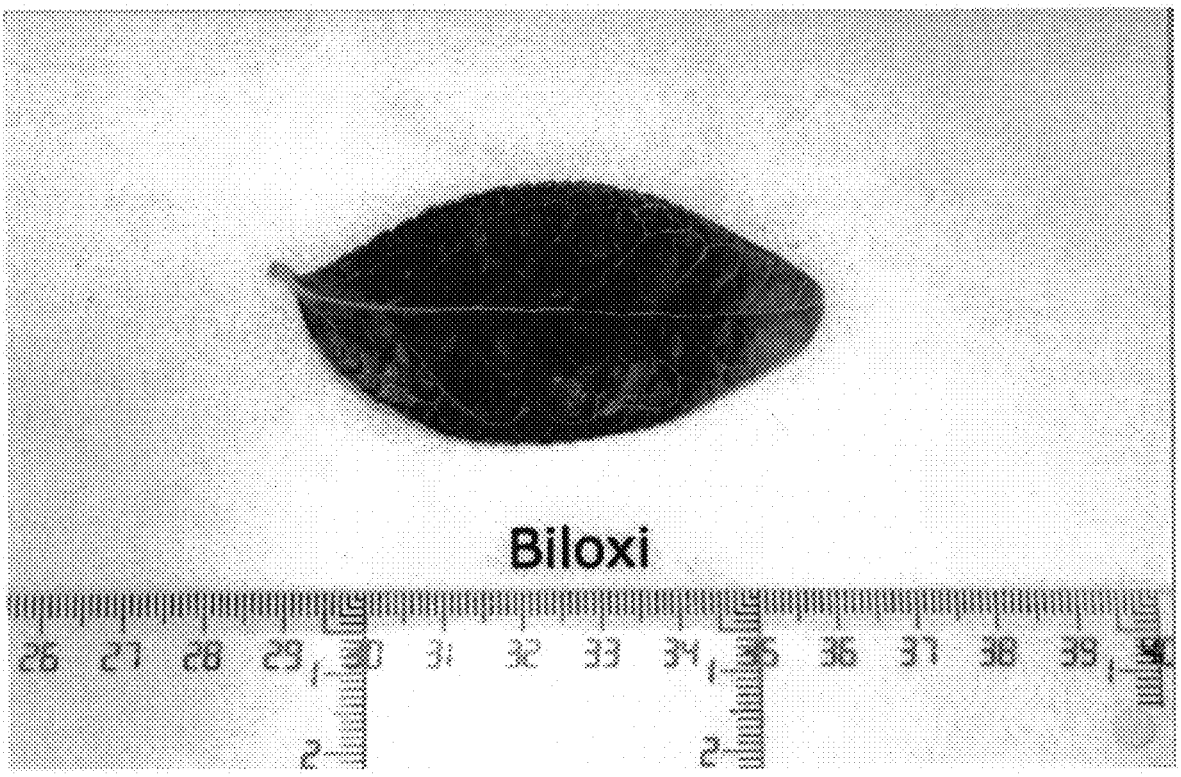
FIG. 14 shows the leaf of blueberry variety 'Biloxi' (unpatented).
Figure 15:
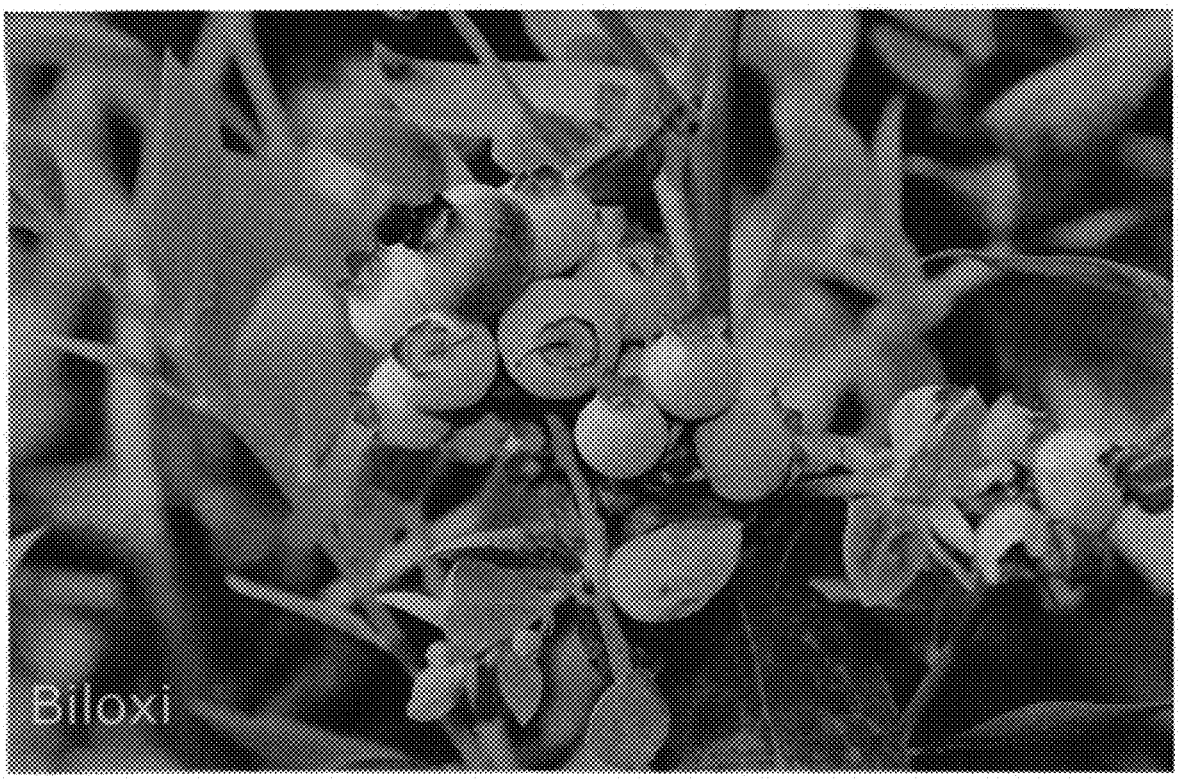
FIG. 15 shows the density of fruit cluster of 'Biloxi' (unpatented) which is higher than the density of fruit cluster of the new variety (designated 15.09.003).
Figure 16:
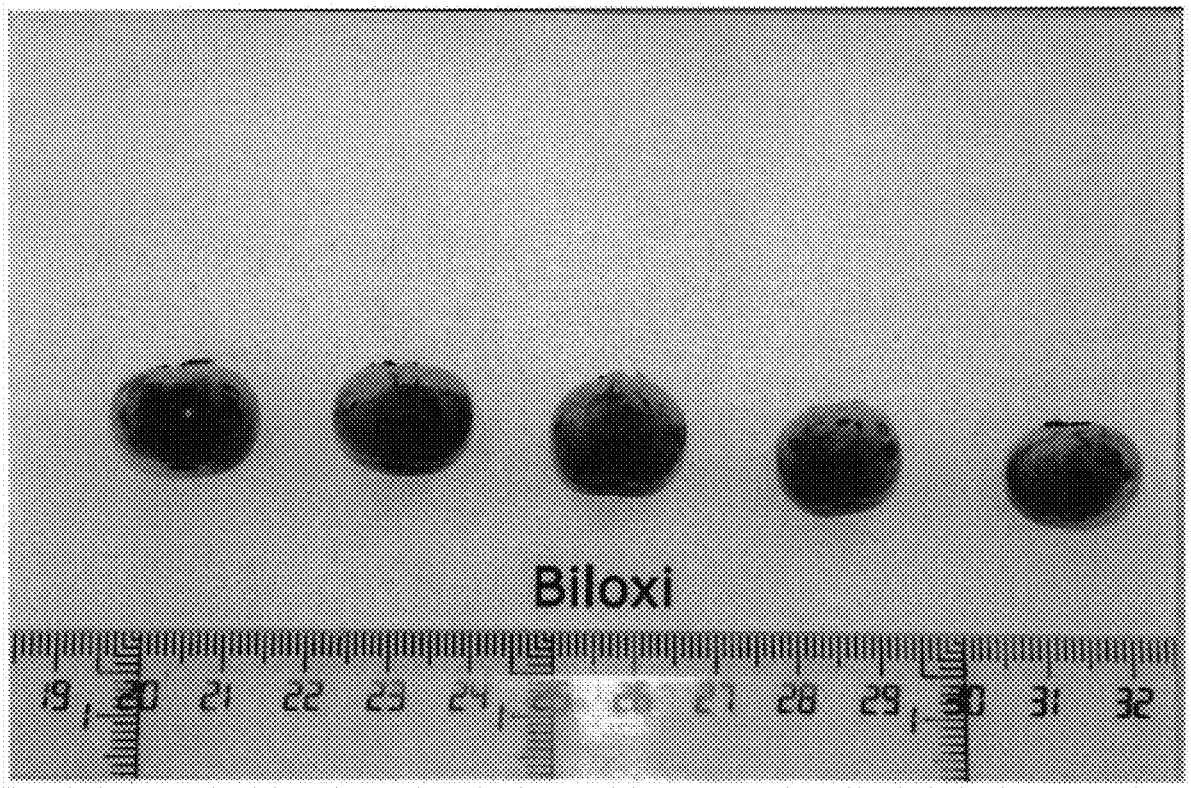
FIG. 16 shows the fruit of blueberry variety 'Biloxi' (unpatented) which exhibits an oblate shape.
Figure 17:
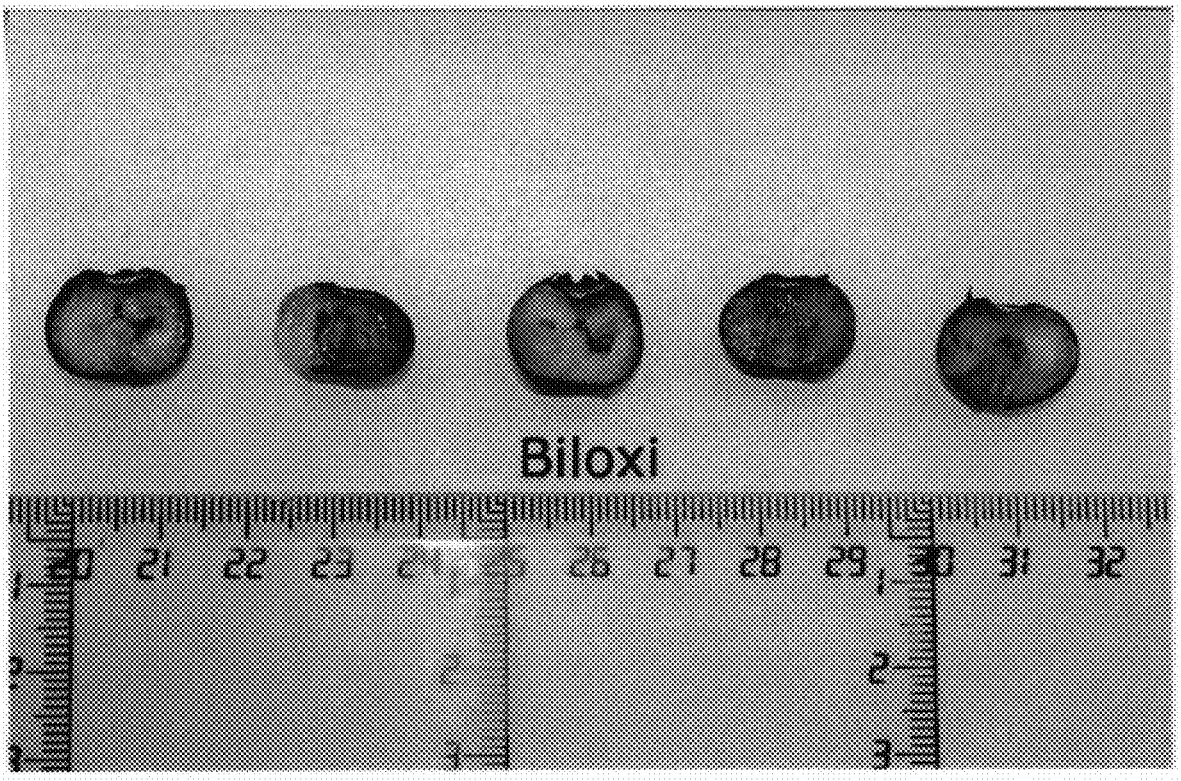
FIG. 17 shows sliced fruits of blueberry variety 'Biloxi' (unpatented) which exhibits a shallow depth of the calyx basin.

The following detailed description of the new variety is based upon observations taken of plants and fruits grown "underglass", i.e. undertunnel, in the farm of La Mogalla in Cartaya (Huelva), Spain, 7° W., 37° N., 45 feet elevation.

The following description is in accordance with UPOV terminology and the color teminology herein is in accordance with The Royal Horticultural Society Colour Chart (R.H.S.C.C.), 3$^{rd}$ edition published in 1995. The color descriptions and other phenotypical descriptions may deviate from the stated values and descriptions depending upon variation in environmental, seasonal, climatic and cultural conditions.

PROPAGATION

The new variety is principally propagated by softwood cuttings. Although propagation by softwood cuttings is presently preferred, other know methods of propagating blueberry plants may be used.

Blueberry root and develop well after transplanting.

GENERAL

'Plablue 1549' is propagated by softwood cuttings. It is a variety with fruit production from beginning January through middle June. It is a self-fertile variety. It produces large quantities of pollen throughout the seasons and pollination is good.

Production: Plants described are from high elevation nursery in Segovia, Spain, 3° 59'W., 41° 22'N., 2742 feet elevation.

Trials pursued in Cartaya (Huelva), Spain.

Date of planting: 14th October.

Number of repetitions: 2

Plants per repetition: 50

TABLE 1

Table 1 shows the accumulated production of fruit (g/plant) of the new variety 'Plablue 1549' when compared to its closest varieties 'Biloxi' and 'Star' (U.S. Plant Pat. No. 10,675).

| Variety | February 27 | March 31 | April 30 | June 22 |
|---|---|---|---|---|
| Plablue 1549 | 1543.00 | 2027.67 | 2821.00 | 4475.00 |
| Biloxi | 191.67 | 477.33 | 905.33 | 2850.00 |
| Star | 0.00 | 757.67 | 1781.73. | 1803.10 |

TABLE 2

Table 2 shows the weight (g/fruit) at three dates of the new variety 'Plablue 1549' when compared to its closest varieties 'Biloxi' and 'Star'.

| Variety | March 31 | April 30 | June 22 |
|---|---|---|---|
| Plablue 1549 | 19.00 | 18.00 | 16.00 |
| Biloxi | 16.00 | 14.00 | 14.00 |
| Star | 18.00 | 18.00 | 17.00 |

**Weight is shown as the average weight per fruit

DETAILED DESCRIPTION OF THE NEW VARIETY

The following additional information is provided to further describe the new variety.

Variety: 'Plablue 1549'. Breeder Ref. 15.10.086.

Latin name: *Vaccinium corymbosum* L.

Common name: Southern highbush blueberry.

Plants are growing in containers of 45 liters of capacity.

Plant:

*Habit*.—Upright.

*Vigor*.—Medium.

*Height of plant*.—About 1.80 to 1.90 m.

*Canopy diameter*.—About 1.20 to 1.3 m.

*Twigginess*.—High.

*Suckering*.—Low.

*Evergreenness*.—Evergreen.

*Chilling requirement*.—Approximately 100-200 hour at temperatures at or below 7° C.

*Cold hardiness*.—Has not been grown in all environments including harsh winter environments. Cold tolerance is expected to be low.

Trunk and Branches:

*Surface texture new wood*.—Smooth.

*Surface texture* 1 *year wood*.—Smooth.

*Surface texture* 2 *years and older wood*.—Rough.

*Diameter new wood*.—About 5.0 to 6.0 mm.

*Diameter* 1 *year wood*.—About 10.0 to 11.0 mm.

*Diameter* 2 *years and old wood*.—About 22.0 to 23.0 mm.

*Color*.—New wood about yellow-green color (RHS Yellow-Green group color near 144 B to 144 A) transitioning to about greyed-orange color (RHS Greyed-Orange group color near 177 C to 177 B) in about 2 year old wood.

Leaf:

*Internode length*.—About 12.5 to 22.0 mm.

*Leaf arrangement*.—Alternate simple.

*Length*.—About 6.8 to 7.2 cm.

*Width*.—About 5.0 to 5.5 cm.

*Leaf shape*.—Elliptic.

*Shape of tip*.—Acute.

*Shape of base*.—Obtuse.

*Shape of margin*.—Entire.

*Venation pattern*.—Reticulate.

*Mature leaf color upperside*.—RHS Green group near 137 C to 137 A.

*Mature leaf color underside*.—RHS Yellow-Green group color near 144 B to 144 A.

*Pubescence upper leaf surface*.—Absent.

*Pubescence under leaf surface*.—Present.

*Pubescence leaf margin*.—Present.

*Precocity*.—New vegetative growth before flowering.

Petiole:

*Length*.—About 2.5 to 3.0 mm.

*Width* (*diameter*).—About 2.5 to 3.0 mm.

*Texture*.—Smooth.

*Color*.—RHS Yellow-Green group color near 145 B to 145 A.

Flower:

*Flower arrangement*.—Compound raceme. Clusters at the end of branches.

*Flower shape*.—Urceolate.

*Flowers per cluster*.—About 7 to 8.

*Flower fragrance*.—Pleasant.

*Immature flower color*.—RHS Orange-Red group color near 35 B to 35 A.

Corolla:

*Length*.—About 8.0 to 9.0 mm.

*Diameter*.—About 8.0 to 9.0 mm.

*Aperture width*.—About 3.0 to 4.0 mm.

*Color*.—RHS Yellow-White group color near 158 C to 158 B.

*Texture*.—Smooth.

Peduncle:

*Length*.—About 17.5 to 18.0 mm.

*Color*.—RHS Yellow-Green group color near 145 B to 145 A.

Pedicel:

*Length*.—About 13.5 to 14.0 mm.

*Color*.—RHS Yellow-Green group color near 145 B to 145 A.

*Calyx (with sepals) diameter*.—8.5 to 9.5 mm.

*Calyx texture*.—Smooth.

*Color center of calyx*.—RHS Green group color near 143 C to 143 B.

*Color sepals*.—RHS Yellow-Geen group color near 145 B to 145 A.

*Attitude of sepals*.—Erect.

*Type of sepals*.—Reflexed.

Stamen:

*Length*.—About 4.5 to 5.0 mm.

*Number per flower*.—About 10 to 11.

*Filament color*.—RHS Yellow-Green group color near 145 D to 145 C.

Style:

*Length*.—About 6.8 to 7.2 mm.

*Color*.—RHS Yellow-Green group color near 145 C to 145 B.

Pistil:

*Length*.—About 8.2 to 8.5 mm.

*Ovary color*.—RHS Yellow-Green group color near 145 D to 145 C.

Anther:

*Length*.—About 2.5 to 3.0 mm.

*Number*.—About 10 to 11.

*Color*.—RHS Greyed-Orange group color near 165 B to 165 A.

Pollen:

*Abundance*.—Medium.

*Color*.—RHS Yellow-Orange group color near 20 C to 20 B.

*Self-compatibility*.—The cultivar has demonstrated a high degree of self-compatibility.

Fruit:

*Fruiting type*.—On one-year-old and current season's shoots.

*Calyx aperture*.—About 5.0 to 6.0 mm.

*Calyx lobes*.—About 4 to 5 lobes.

*Calyx depth*.—About 2.6 to 2.9 mm.

*Pedicel length*.—About 10.5 to 11.0 mm.

*Pedicel surface texture*.—Smooth.

*Peduncle length*.—About 12.5 to 13.0 mm.

*Peduncle surface texture*.—Smooth.

*Berries per cluster*.—About 6 to 8.

*Berry detachment*.—Easy.

*Weight*.—About 16 to 19 grs.

*Height*.—About 14.0 to 15.0 mm.

*Width*.—About 19.0 to 20.0 mm.

*Shape*.—Round.

*Color with wax*.—RHS Violet-Blue group color near 97 D to 97 C.

*Color with wax removed*.—RHS Black group color near 202 A.

*Persistent wax*.—Moderate.

*Surface wax abundance*.—Moderate.

*Flesh color*.—RHS Yellow-Green group color near 149 D to 149 C.

*Pedicel scar*.—About 0.9 to 1.3 mm.

*Firmness*.—0.8 Kg. Firmness: It is the fruit's resistance to penetration measured in Kilograms (Kg). The measure given has been obtained by the penetrometer ROZE Mod. Arbelette, with a 20 $mm^2$ section head.

*Texture of flesh*.—Soft and juicy.

Seed:

*Color*.—RHS Greyed-Orange group color near 165 B to 165 A.

*Length*.—About 1.0 to 2.0 mm.

*Width*.—About 0.90 to 1.0 mm.

*Weight*.—About 0.3 to 0.4 mg.

*Seeds per berry*.—About 16 to 20.

General: The growing period in Huelva, Spain, where the observations on primocane production were made, is between about November 20 and June 22 of the following year. 'Plablue 1549' is a blueberry variety that benefits from induction to flowering by chilling, usually a few hours (approximately 100-200 hours) are sufficient, preferably at temperatures of 7° C. or less. Normally, the minimum number of hours is accumulated in the field during several days. 'Plablue 1549' is a variety with consistent fruit production beginning in on first days of January and ending at the middle of June. After planting as aforesaid, plants are grown in containers under tunnel. Water and fertilizer were applied through drip irrigation.

Date of planting: About October 15 in the farm of La Mogalla, in Cartaya (Huelva), Spain, about 7° W, 37° N, 45 feet elevation. Time of flowering data: 10% flowering about October 18. First mature fruits are about January 4 (15-20 g/plant), with a maximum production at the middle of May.

Storage qualities: 'Plablue 1549' fruit maintains their quality characteristics when keeping them in a frigo chamber at temperatures of about 2° C. for a duration of about 24 days. The fruit's color remains substantially the same. Shelf life of 'Plablue 1549' is good.

Use/market: The berries of 'Plablue 1549' are suitable for consumption as fresh fruit. Also, they are amenable to processing.

Disease resistance: No particular sensitivity to any disease or pest has been observed for 'Plablue 1549'

I claim:

1. A new and distinct blueberry plant of the variety substantially as shown and described.

* * * * *